United States Patent
Allred

(10) Patent No.: US 9,616,005 B2
(45) Date of Patent: *Apr. 11, 2017

(54) METHODS FOR MANUFACTURING DENTAL BLEACHING DEVICES

(71) Applicant: ULTRADENT PRODUCTS, INC., South Jordan, UT (US)

(72) Inventor: Peter M. Allred, Bluffdale, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,235

(22) Filed: Mar. 29, 2016

(65) Prior Publication Data

US 2016/0206524 A1    Jul. 21, 2016

Related U.S. Application Data

(63) Continuation of application No. 14/741,206, filed on Jun. 16, 2015, now Pat. No. 9,295,633, which is a
(Continued)

(51) Int. Cl.
*A61K 8/22* (2006.01)
*A61K 8/38* (2006.01)
(Continued)

(52) U.S. Cl.
CPC .................. *A61K 8/22* (2013.01); *A61K 8/25* (2013.01); *A61K 8/34* (2013.01); *A61K 8/345* (2013.01);
(Continued)

(58) Field of Classification Search
CPC ........................................................ A61K 8/22
See application file for complete search history.

(56) References Cited

U.S. PATENT DOCUMENTS

| 4,592,487 A | 6/1986 | Simon et al. |
| 5,130,124 A | 7/1992 | Merianos et al. |

(Continued)

FOREIGN PATENT DOCUMENTS

| EP | 1504753 | 2/2005 |
| JP | 59-128330 | 7/1984 |

OTHER PUBLICATIONS

Cabot (www.cabot-corp.com, 2001).*
(Continued)

*Primary Examiner* — Benjamin Packard
(74) *Attorney, Agent, or Firm* — Workman Nydegger

(57) ABSTRACT

Method of manufacturing a dental bleaching device including a dental bleaching composition and a barrier layer. The bleaching composition includes a dental bleaching agent, a generally linear high molecular weight polyvinyl pyrrolidone (PVP) and/or polyethylene oxide (PEO) tissue adhesion agent that imparts adhesiveness, a rheology-modifying agent such as fumed silica or fumed alumina that reduces or eliminates stringiness otherwise caused by the high molecular weight PVP and/or PEO, and a carrier. The barrier layer may comprise a dental tray or strip. Dental treatment devices including a barrier layer and a quantity of the dental bleaching composition positioned adjacent to the barrier layer.

25 Claims, 5 Drawing Sheets

Related U.S. Application Data continuation of application No. 11/460,016, filed on Jul. 26, 2006, now Pat. No. 9,067,082.

(51) Int. Cl.

| | | |
|---|---|---|
| *A61K 8/81* | (2006.01) | |
| *A61K 8/86* | (2006.01) | |
| *A61Q 11/00* | (2006.01) | |
| *A61Q 11/02* | (2006.01) | |
| *A61K 8/25* | (2006.01) | |
| *A61K 8/34* | (2006.01) | |

(52) U.S. Cl.
CPC .............. *A61K 8/38* (2013.01); *A61K 8/8147* (2013.01); *A61K 8/8176* (2013.01); *A61K 8/86* (2013.01); *A61Q 11/00* (2013.01); *A61Q 11/02* (2013.01); *A61K 2800/592* (2013.01); *A61K 2800/87* (2013.01); *A61K 2800/88* (2013.01); *A61K 2800/92* (2013.01)

(56) References Cited

U.S. PATENT DOCUMENTS

| | | |
|---|---|---|
| 5,270,033 A | 12/1993 | Montgomery |
| 5,292,502 A | 3/1994 | Burke et al. |
| 5,631,000 A | 5/1997 | Pellico et al. |
| 5,670,138 A | 9/1997 | Venema et al. |
| 5,891,453 A | 4/1999 | Sagel et al. |
| 6,086,854 A | 7/2000 | Arnold |
| 6,126,922 A | 10/2000 | Rozzi et al. |
| 6,221,341 B1 | 4/2001 | Montgomery |
| 6,239,090 B1 | 5/2001 | Marquis et al. |
| 6,294,594 B1 | 9/2001 | Borja et al. |
| 6,500,408 B2 | 12/2002 | Chen |
| 6,682,722 B2 | 1/2004 | Majeti et al. |
| 6,696,045 B2 | 2/2004 | Yue et al. |
| 6,702,999 B2 | 3/2004 | Lawlor |
| 6,730,316 B2 | 5/2004 | Chen |
| 6,860,736 B2 | 3/2005 | Allred et al. |
| 6,964,571 B2 | 11/2005 | Andersen et al. |
| 6,981,874 B2 | 1/2006 | Allred et al. |
| 6,986,883 B2 | 1/2006 | Pellico |
| 6,997,708 B2 | 2/2006 | Allred et al. |
| 7,011,523 B2 | 3/2006 | Allred et al. |
| 7,048,543 B2 | 5/2006 | Allred et al. |
| 7,052,275 B2 | 5/2006 | Allred et al. |
| 7,056,118 B2 | 6/2006 | Allred et al. |
| 7,059,857 B2 | 6/2006 | Allred et al. |
| 7,059,858 B2 | 6/2006 | McLean et al. |
| 7,060,256 B2 | 6/2006 | Pellico |
| 7,074,042 B2 | 7/2006 | Allred et al. |
| 2002/0197214 A1 | 12/2002 | Bublewitz et al. |
| 2003/0036493 A1 | 2/2003 | Alam et al. |
| 2004/0028624 A1 | 2/2004 | Bublewitz et al. |
| 2004/0101496 A1 | 5/2004 | Chen |
| 2004/0219190 A1 | 11/2004 | Kosti |
| 2004/0223923 A1 | 11/2004 | Chen |
| 2004/0241620 A1* | 12/2004 | Allred ...................... A61C 5/00 433/215 |
| 2005/0008584 A1 | 1/2005 | Montgomery |
| 2005/0031552 A1 | 2/2005 | Mori et al. |
| 2005/0036956 A1 | 2/2005 | Fei et al. |
| 2005/0069502 A1 | 3/2005 | Chopra et al. |
| 2005/0113510 A1 | 5/2005 | Feldstein et al. |

OTHER PUBLICATIONS

Cabot Corp., "CAB-O-SiI fumed silica in Cosmetic and Personal Care Products", www.lotioincrafter.com/reference/tech_data_silica.pdf, 2001, pp. 1-7. (The month of Publication is irrelevant since the year of Publication is clearly prior to the filing of the Application).
U.S. Appl. No. 11/460,016, Nov. 3, 2008, Office Action.
U.S. Appl. No. 11/460,016, Apr. 10, 2009, Office Action.
U.S. Appl. No. 11/460,016, Sep. 1, 2009, Office Action.
U.S. Appl. No. 11/460,016, Apr. 9, 2010, Office Action.
U.S. Appl. No. 11/460,016, Sep. 24, 2010, Office Action.
U.S. Appl. No. 11/460,016, Jan. 13, 2011, Office Action.
U.S. Appl. No. 11/460,016, Apr. 27, 2015, Notice of Allowance.
U.S. Appl. No. 14/741,206, Jul. 17, 2015, Office Action.
U.S. Appl. No. 14/741,206, Nov. 27, 2015, Notice of Allowance.

* cited by examiner

METHODS FOR MANUFACTURING DENTAL BLEACHING DEVICES

CROSS REFERENCE TO RELATED APPLICATION

This application is a continuation of U.S. patent application Ser. No. 14/741,206, filed Jun. 16, 2015, which is a continuation of U.S. patent application Ser. No. 11/460,016, filed Jul. 26, 2006, the disclosures of which are incorporated herein in their entirety.

BACKGROUND OF THE INVENTION

1. The Field of the Invention

The present invention is in the field of dental bleaching compositions, devices and methods for whitening a person's teeth. The invention relates to dental bleaching compositions having a high level of rheological stability, stickiness, low stringing tendency, and high internal cohesiveness.

2. The Relevant Technology

To achieve whiter teeth, people often have their teeth covered with veneers or chemically bleached. A conventional in-office bleaching process generally involves: (1) making an alginate impression of the patient's teeth; (2) making a stone cast or model of the impression; (3) vacuum forming a dental tray from the model, usually from a heated sheet of thin ethyl vinyl acetate (EVA) material, (4) trimming the upper tray rim to exclude gingival coverage, (5) introducing a bleaching gel into the tray, and (6) placing the tray over the teeth to be bleached for a suitable time period to effect tooth bleaching.

Because of the time and cost associated with forming customized trays, less time consuming and costly alternatives have been developed. Examples include boil and bite trays and non-custom trays, both of which tend to bulky and uncomfortable, flexible strips, which have a tendency to slip off the teeth, and paint-on bleaching compositions, which are directly exposed to saliva in a person's mouth.

In order to adhere a dental bleaching composition to a person's teeth, a tackifying agent is typically used. A common tackifying agent is carboxypolymethylene, an acidic polyacrylic acid polymer cross-linked with polyallyl sucrose. According to U.S. Pat. No. 6,500,408 to Chen, carboxypolymethylene allegedly causes tooth irritation because of (i) its ability to etch teeth because of its generally acidic nature and (ii) its tendency to chelate calcium ions found in teeth. In order to avoid such problems, Chen teaches the use of polyvinylpyrrolidone (PVP) polymers, which are neither acidic nor are believed to bind calcium. Besides carboxypolymethylene, Chen also disparages the use of fumed silica. Col. 3, lines 37-50. It is known that including fumed silica in an amount so as to adequately thicken and form a firm bleaching gel can greatly reduce the ability of a peroxide bleaching agent to bleach teeth. Fumed silica has an extremely high surface area, is highly hydrophilic and therefore binds strongly to water. By strongly binding to the water, fumed silica included in an amount sufficient to form a firm gel inhibits the passage of water into the tooth surfaces to be bleached. Because water is generally necessary to carry the peroxide bleaching agent into the tooth surfaces to be bleached, fumed silica that binds water indirectly inhibits passage of the bleaching agent into the tooth surfaces, greatly inhibiting tooth bleaching. For this reason, Chen teaches the desirability of using PVP polymers as the sole or primary thickening agent.

The problem with PVP and other linear polymers is they tend to form highly stringy dental bleaching compositions when included in an amount sufficient to yield a sticky, viscous composition that is able to adhere a dental tray to a person's teeth. This can greatly complicate the process of filling a dental tray with such compositions on a mass production scale. Moreover, even though compositions that include high amounts of PVP can be very adhesive, they may still lack sufficient thickness or viscosity to avoid running out of a pre-filled dental tray. Stickiness does not necessarily correlate with sufficient viscosity and yield stress to avoid running from a dental tray. A highly sticky Newtonian fluid may nevertheless be able to run out over time due to the force of gravity.

In general, the tendency of high potency dental bleaching compositions to run out of a pre-filled dental tray increases over time due to the tendency of polymeric tackifying agents such as carboxypolymethylene and PVP to lose viscosity and yield stress over time. This may be due to small but significant attack by the dental bleaching agent, typically a peroxide, on the tackifying polymer when included in high concentrations. Even though a dental bleaching composition may be sufficiently thick and viscous to avoid running out of the dental tray when first placed therein, it may nevertheless become runny over time, thereby critically reducing shelf-life in the case of over-the-counter products that must have a shelf life of several months or years. As a result, high shelf-like bleaching products typically have lower levels of peroxide to avoid viscosity breakdown and the tendency to become runny.

Although polymeric thickeners such as polysaccharide gums (e.g., xanthan gum) and carboxymethyl cellulose can be used to enhance the body and yield stress of dental bleaching compositions, they also create long-term stability issues. Such polymers tend to break down in the presence of highly concentrated peroxide bleaching agents. Worse, such polymers can react with peroxide bleaching agents such as hydrogen peroxide and form reactive organic peroxide species that can attack a person's gums and also the cross-linkages within carboxypolymethylene, which can greatly reduce its tackifying and thickening ability. Such thickeners are therefore only suitable for low level bleaching compositions containing 5% or less peroxide bleaching agent.

In view of the foregoing, there is a need to provide improved bleaching compositions that are sticky and viscous while having improved processing ability and long-term rheological stability. Such compositions would be particularly well-suited for use in manufacturing pre-filled dental bleaching devices (e.g., trays and strips).

BRIEF SUMMARY OF THE INVENTION

The present invention is directed to dental bleaching compositions having superior adhesiveness to dental tissues, but with reduced stringiness, increased internal cohesiveness, and increased long-term rheological stability. The dental bleaching composition includes a dental bleaching agent, a tissue adhesion agent, a rheology-modifying agent, and a solvent or carrier. The invention also relates to treatment devices which include a barrier layer and a quantity of the adhesive dental bleaching composition disposed adjacent to the barrier layer, as well as kits and methods for use in bleaching a person's teeth.

According to one currently preferred embodiment, the tissue adhesion agent comprises one or more high molecular weight linear polymers such as polyvinyl pyrrolidone (PVP) and/or polyethylene oxide (PEO). While PVP and/or PEO at high molecular weight provide superior adhesion to teeth compared to other known gel-forming agents, the generally linear molecular structure of PVP and PEO yields bleaching compositions that can be extremely stringy and difficult to handle when included in concentrations of about 15% by weight and higher. This can greatly interfere with the manufacture of pre-filled dental bleaching trays or strips, particularly while placing the dental bleaching composition adjacent to the barrier layer. It is difficult to sever a stringy composition in the dispensing nozzle from the bead placed against the barrier layer. In some cases, long, stringy, spider web-like masses can form, creating a messy product and manufacturing station. In addition, while PVP and PEO yield compositions that are very adhesive, such compositions can be runny and have an essentially Newtonian rheology, particularly over long periods of time (e.g., 3 months or more).

It has unexpectedly been found that including a solid particulate rheology-modifying agent such as fumed silica and/or fumed alumina in a relatively small amount not only increases the cohesiveness and reduces the runniness of dental bleaching compositions that contain PVP and/or PEO it also reduces or eliminates the stringiness otherwise caused by PVP and/or PEO. Because fumed silica is not a polymer, its ability to thicken a dental bleaching composition does not diminish over time even in the presence of a highly concentrated dental bleaching agent. Moreover, including a relatively small amount of fumed silica greatly reduces the tendency of fumed silica to inhibit dental bleaching by binding to water necessary to carry the bleaching agent into the tooth surfaces to be bleached (e.g., water in the bleaching composition itself and/or in a person's saliva adjacent to the person's teeth).

The high molecular weight, generally linear polymeric tissue adhesion agents (e.g., PVP and/or PEO) used within the scope of the invention preferably have a molecular weight of at least about 500,000. At molecular weights substantially below 500,000, the adhesive and viscosity building properties of PVP and PEO are greatly reduced. For example, at molecular weights of 300,000 and below, a precipitous drop off in the adhesive and viscosity building properties of PVP was found. Compositions made therewith lack adequate adhesiveness and tend to be very runny. At molecular weights of at least about 1,000,000, the adhesive properties of PVP and/or PEO are optimal and therefore most preferred.

Based on testing compositions having PVP with molecular weights of 1,000,000 and above compared to compositions having PVP with molecular weights of 300,000 and below, the adhesive and viscosity building properties of PVP and PEO are believed to dramatically increase as the molecular weight is increased significantly above 300,000. Thus, it is currently preferred for PVP, PEO and like polymers to have a molecular weight of at least about 500,000, more preferably at least about 650,000, even more preferably at least about 800,000, and most preferably a molecular weight of at least about 1,000,000.

Though increasing the molecular weight greatly improves the adhesive properties of PVP and PEO, which is beneficial, it also increases the stringiness of dental bleaching compositions made therefrom, which is detrimental. This is believed to be due to the generally linear molecular structure of PVP and PEO. It has been found that dental bleaching compositions that include high molecular weight PVP and/or PEO, particularly at the more preferred molecular weights and higher concentrations (i.e., 15% and above), can be quite difficult to handle. Such compositions tend to break apart into a stringy mess during handling, creating a spider web-like bundle rather than a coherent mass. There is therefore a need to increase the internal cohesion and yield stress of dental bleaching compositions that include high molecular weight PVP and/or PEO in concentrations of about 15% by weight or greater, while maintaining adequate adhesiveness, in order to improve handling during manufacture and use.

It has unexpectedly been found that including a rheology-modifying agent such as fumed silica and/or fumed alumina in relatively small amounts (i.e., too small to yield a stiff gel by itself) so as to reduce or eliminate runniness also yields a much more coherent mass with little or no stringiness. This provides a greater degree of control while dispensing and otherwise handling the composition. The dental bleaching composition can be dispensed onto a barrier layer and then severed without forming long, unwieldy web-like strings when separating the dispensing nozzle or tip from the composition placed on the barrier layer. The rheology-modifying agent also significantly reduces the tendency of the bleaching composition to run off the barrier layer where initially placed.

The rheology-modifying agent alters the physical properties of the dental bleaching composition by imparting Binghamian plastic-like properties while reducing the Newtonian fluid properties. In other words, including fumed silica and/or fumed alumina imparts yield stress, resulting in a composition which will typically only flow under a minimum sufficient yield pressure. In the absence of such minimum pressure the composition retains its shape. If the yield stress imparted by the rheology-modifying agent equals or exceeds the force of gravity, the dental bleaching composition will remain where placed without significant running. Shape retention of the bleaching composition is a distinct advantage when handling the composition (e.g., when applying the composition to a dental bleaching tray or other barrier layer and while shipping and storing the bleaching devices).

Another advantage of including fumed silica is its ability to provide long-term rheological stability to a dental bleaching composition. Tissue adhesion agents comprising cross-linked polymers, such as carboxypolymethylene, do not have the same level of stringiness problems associated with linear polymers, as discussed above. They also tend to yield dental bleaching compositions having high viscosity and low runniness that initially remain where placed adjacent to a barrier layer. Nevertheless, such polymers can be even more susceptible to breakdown and attack in the presence of highly concentrated peroxide bleaching agents. Over time, dental bleaching compositions that may have high initial viscosity and yield stress can break down over time, yielding a runny composition than can run off the barrier layer. This greatly reduces shelf life. Including a relatively small concentration of fumed silica (less than about 8.5% by weight) has been found to greatly stabilize the rheology of such compositions over time, thereby increasing their shelf-life.

High molecular weight PEO is capable of providing a high degree of tackiness and adhesiveness, although PEO has been found to be less adhesive but even more difficult to handle compared to PVP of the same molecular weight. In other words, while it has been found, for example, that PEO having a molecular weight of about 1.3 million can be used as an adhesive agent, PVP having a molecular weight of about 1.3 million is more preferred because it provides more adhesiveness while also having somewhat improved handling properties. For this reason, PVP is particularly preferred as the adhesive agent, although it is within the scope of the invention to use PEO.

An inventive kit according to the invention includes a barrier layer and a dental bleaching composition, which is comprised of a dental bleaching agent, a tissue adhesion agent comprising PVP and/or PEO having a molecular weight of at least about 500,000 and/or carboxypolymethylene or other cross-linked polymeric thickening agent, a rheology-modifying agent, and a solvent or carrier. In such a kit, the user may apply a quantity of the dental bleaching composition to the barrier layer so as to form a dental bleaching device. Alternatively, the dental bleaching composition may be pre-applied to the barrier layer during manufacture and packaging. In either case, the user simply positions the bleaching device comprising the barrier layer and bleaching composition over the teeth to be bleached. Because of the long-term rheological stability of the inventive bleaching composition, even with highly concentrated peroxide bleaching agent, they can more consistently hold the barrier layer in place compared to conventional bleaching strips or pre-filled bleaching trays. Moreover, the rheology-modifying agent helps maintain the composition as a coherent mass so as to not run off where placed on the barrier layer over time.

Another kit according to the invention includes individual bleaching devices pre-packaged together, typically within a sealed package. In one embodiment, a pair of bleaching devices designed for placement over the upper and lower dental arches can be pre-packaged together. Multiple pairs of pre-packaged bleaching devices can be packaged together so as to provide a bleaching regimen of a desired number of treatments.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1A:
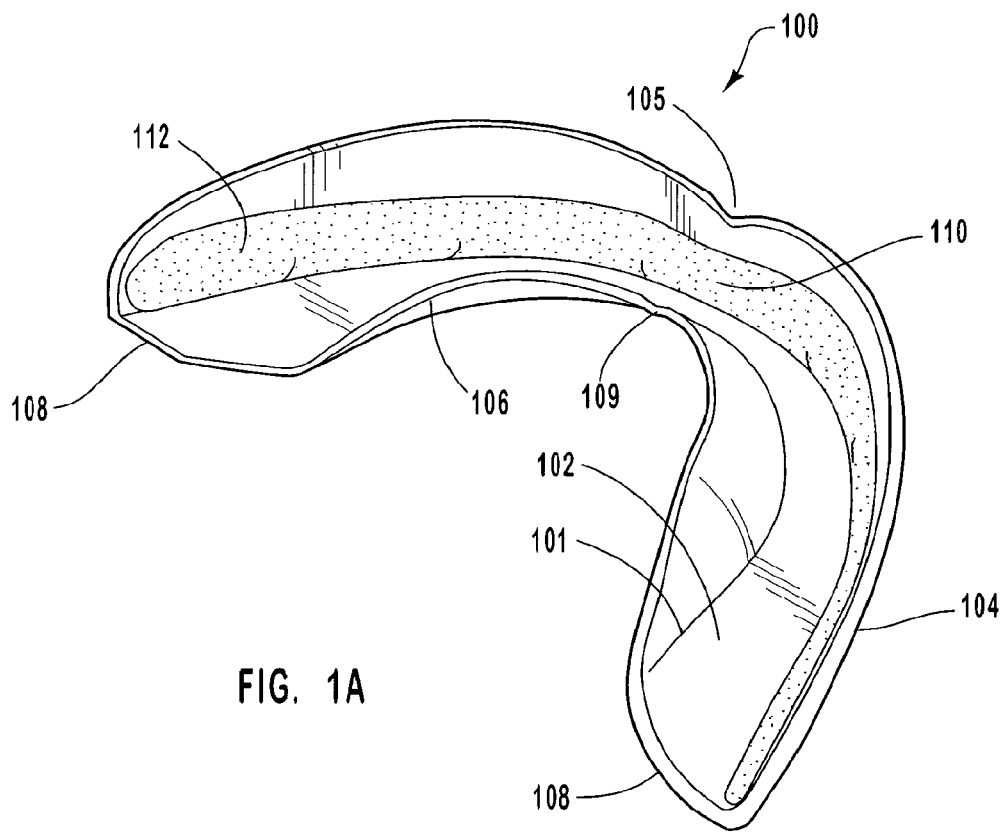
FIG. 1A is a perspective view of an exemplary embodiment of a dental treatment device configured for placement over the upper dental arch, the device including a barrier layer and a dental bleaching composition disposed adjacent to the barrier layer.

The present invention involves dental bleaching compositions which include a tissue adhesion agent, such as high molecular weight polyvinyl pyrrolidone (PVP) and/or polyethylene oxide (PEO), in combination with an amount of a rheology-modifying agent that reduces or eliminate the stringiness caused by PVP and/or PEO while also reducing the runniness and increasing the internal cohesiveness of dental bleaching compositions that include PVP and/or PEO in combination with a solvent or carrier. The present invention also involves adding a relatively small quantity of fumed silica or other finely divided particulate rheology-modifying that does not break down in the presence of highly concentrated peroxide bleaching compositions in order to maintain long-term rheological stability of compositions that include a polymeric tissue adhesion agent (e.g., PVP, PEO and carboxypolymethylene) that is susceptible to losing viscosity and thickness over time when in the presence of a highly concentrated peroxide dental bleaching agent.

The present invention understands the tradeoff between increasing the molecular weight and/or concentration of PVP and/or PEO in order to increase the adhesive properties of dental bleaching compositions and the tendency of such compositions to be highly stringy and difficult to handle. In has unexpectedly been found that the stringiness of dental bleaching compositions formed using high molecular weight PVP and/or PEO can be reduced, while maintaining a high level of adhesiveness and internal cohesion, by including an appropriate quantity of a particulate rheology-modifying agent such as fumed silica or fumed alumina. The fumed silica or other finely divided particulate rheology-modifying agent maintains long-term rheological stability so as to prevent or inhibit the composition from running off the barrier layer over time.

Dental bleaching devices and kits include a barrier layer and a dental bleaching composition that includes a high molecular weight linear polymeric tissue adhesion agent such as PVP and/or PEO and/or a cross-linked polymeric tissue adhesion agent such as carboxypolymethylene and a rheology-modifying agent (e.g., fumed silica and/or fumed alumina). Although dental bleaching compositions that include PVP and/or PEO have superior tissue adhesion properties, such compositions can be difficult to handle. Dental bleaching compositions that include high molecular weight PVP and/or PEO in quantities of 15% or more without a rheology-modifying agent such as fumed silica or fumed alumina tend to break apart during manufacture of bleaching devices into a stringy mess comprising spider web-like strings. Such handling disadvantage is even more pronounced with compositions that include very high molecular weight PEO.

The inclusion of an adequate amount of a rheology-modifying agent, such as fumed silica or fumed alumina, has been found to yield a more coherent mass, reducing or eliminating the stringiness of the composition. This characteristic provides more control for dispensing the composition into a tray shaped barrier layer, applying a layer of composition against a barrier layer strip or otherwise handling the composition whether such handling occurs during manufacture or just prior to use by the end user. For example, when dispensed from a nozzle of a loading machine against a barrier layer, the dental bleaching composition can be applied as a single coherent mass and then severed from the dispensing tip, nozzle, syringe, or squeeze tube without forming spider web-like strings. The rheology-modifying agent also yields a composition having increased long-term cohesiveness and reduced tendency to run from where placed on the barrier layer. This greatly increases shelf-life and is an advantage regardless of the polymeric tissue adhesion agent that is used.

The terms "stringy" and "stringiness" refer to dental bleaching compositions that form an elongated string of at least 1 cm under elastic tension when dispensed from a 5 mm nozzle during manufacture of a pre-filled bleaching tray, or a 2 mm syringe tip when applied by an end user (e.g., while separating the portion of bleaching composition that remains in the nozzle or tip of the dispensing apparatus from a bead of composition applied to a barrier layer).

The terms "runny" and "runniness" refer to the tendency of a dental bleaching composition to drip or run off of a barrier layer rather than remaining as a coherent bead of material that stays substantially where placed.

The terms "cohesion", "cohesiveness" and "coherent" refer to a dental bleaching composition having sufficiently high yield stress and Binhamian plastic properties as to substantially remain in the shape as initially placed on a barrier layer during formation of a dental bleaching device (e.g., a continuous bead or series of discontinuous beads).

The term "barrier layer", as used herein, refers to one or more layers of a moisture-resistant material that protects the bleaching composition from ambient moisture and saliva found within a person's mouth when the dental bleaching device is placed over the person's teeth. The barrier layer may also serve to protect the bleaching composition from moisture or other contaminants during storage and prior to use. The barrier layer may be in any desired form including, but not limited to, a dental treatment tray or a flexible strip of material having no permanent shape.

The term "molecular weight", as used herein, refers to number average molecular weight expressed in Daltons unless otherwise specified.

II. Adhesive Dental Bleaching Compositions

Adhesive dental bleaching compositions according to the invention include a dental bleaching agent, a tissue adhesion agent comprising high molecular weight PVP and/or PEO in an amount so as to yield a composition that is very sticky and adhesive to teeth, a rheology-modifying agent in an amount so as to reduce or eliminate stringiness otherwise caused by the PVP and/or PEO in the absence of the rheology-modifying agent, and a solvent or carrier. Alternatively, the tissue adhesion agent may be included in an amount that does not cause stringiness and/or comprise carboxypolymethylene in combination with the rheology-modifying agent in order to increase the yield stress and maintain long-term rheological stability of the composition so that the composition will not run significantly but remain next to a barrier layer where placed. The composition may optionally include other components as desired to yield a dental bleaching composition having desired properties.

A. Dental Bleaching Agents

Dental bleaching agents typically include a peroxide or peroxy compound. A common dental bleaching agent that is known to bleach teeth and that has been found to be safe for oral use is hydrogen peroxide. However, hydrogen peroxide does not itself exist in a stable form free in nature, but only as an aqueous solution or as a complex. Hydrogen peroxide complexes are typically more stable than aqueous hydrogen peroxide, though they may dissociate into hydrogen peroxide and the complexing salt when mixed with water. Even when added to water, complexed hydrogen peroxide is often preferred because they are a solid at room temperature and therefore easier to handle in processes where it is desired to meter out a solid powder rather than a liquid.

Non-limiting examples of complexed hydrogen peroxide include carbamide (or urea) peroxide and metal perborates. Other bleaching agents that can be used to bleach teeth include, but are not limited to, metal percarbonates, peroxides (e.g., calcium peroxide and/or sodium peroxide), chlorites, and hypochlorites, peroxy acids, and peroxy acid salts.

Bleaching agents within the dental bleaching compositions according to the invention can have any desired concentration, e.g., between 1-90% by weight of the dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The one or more bleaching agents are preferably included in an amount in a range of about 5% to about 80% by weight of the dental bleaching composition, more preferably in a range of about 10% to about 60% by weight of the dental bleaching composition, and most preferably in a range of about 15% to about 50% by weight of the dental bleaching composition.

B. Tissue Adhesion Agents

Tissue adhesion agents within the scope of the invention include high molecular weight PVP and/or PEO, i.e., having a molecular weight greater than about 500,000. Utilizing PVP and/or PEO having a molecular weight greater than about 500,000 provides a very adhesive composition which reliably adheres the barrier layer to the person's teeth so as to better maintain the bleaching composition between the barrier layer and the teeth being bleached rather than diffusing into the surrounding oral cavity. This, in turn, promotes better tooth whitening and reduces irritation to surrounding oral tissues and/or at least some of the bad taste normally associated with dental bleaching. The PVP and/or PEO thickening agent will more preferably have a molecular weight greater than about 650,000, even more preferably greater than about 800,000, and most preferably greater than about 1,000,000. The preferred ranges were determined and/or extrapolated by comparing dental bleaching compositions that included PVP having a molecular weight of at least about 1,000,000 with compositions that included PVP having a molecular weight of 300,000 or less. It was noted that reducing the molecular weight below 300,000 caused a precipitous drop-off in tackiness, viscosity and adhesive ability. Above a MW of 300,000 (i.e., 1,000,000 or more) it was determined that the tackiness, viscosity and adhesive ability dramatically improved.

Notwithstanding the improved adhesive properties as the molecular weight of generally linear molecules of PVP and/or PEO increase, compositions made therewith have been found to have increased stringiness and poorer handling properties (e.g., as result of forming web-like strings during placement of the dental bleaching composition adjacent to the barrier layer), particularly at concentrations of 15% and above. Although PEO may be used as an adhesive agent, it has been found that for the same molecular weight, PEO is less sticky and even more difficult to handle than PVP. For this reason, PVP is currently preferred as between PVP and PEO.

Both PVP and PEO are characterized as having long, substantially straight-chained polymer structures. It is believed that this straight-chain characteristic may be at least partially responsible for both the beneficial adhesive properties, on the one hand, and the propensity for compositions including such tissue adhesion agents to be stringy and therefore very difficult to handle (i.e., by easily breaking apart into a stringy, spider web-like mess during placement adjacent to the barrier layer). The inventor has therefore discovered that there is a tradeoff between increasing adhesiveness, on the one hand, and a concomitant increase in stringiness and poor handling, on the other, as the molecular weight and/or concentration of PVP and/or PEO is increased. It is for this reason that the invention also utilizes a rheology-modifying agent in an amount so as to control both the stringiness and runniness of compositions that include high molecular weight PVP and/or PEO.

One particularly preferred example of a PVP polymer that can be used in formulating bleaching compositions according to the invention is Kollidon 90 F, a PVP polymer having a molecular weight of about 1.3 million.

One particularly preferred example of a PEO polymer that can be used in formulating bleaching compositions according to the invention is POLYOX, a PEO polymer having a molecular weight of about 1.3 million made by Union Carbide.

Other tissue adhesion agents may be used in addition to or instead of PVP and PEO within the scope of the invention. These include, but are not limited to, carboxypolymethylene (e.g., CARBOPOL, sold by Novean, Inc.), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, and the like. Such thickening agents, while not imparting stringiness like linear polymers such as PVP and PEO, are even more susceptible than PVP and PEO to losing viscosity and yield stress in the presence of highly concentrated peroxide bleaching agent (i.e., 15% by weight or more hydrogen peroxide or hydrogen peroxide equivalents). For this reason, PVP and PEO are preferred over such materials.

The high molecular weight PVP and/or PEO is preferably included in an amount comprising at least about 5% by weight of the dental bleaching composition, more preferably at least about 10% by weight of the bleaching composition, and most preferably at least about 15% by weight of the bleaching composition. In one particularly preferred embodiment, the high molecular weight PVP and/or PEO is included in a range of about 15% to about 25% by weight of the dental bleaching composition.

Cross-linked polymeric thickening agents such as carboxypolymethylene are preferably included in an amount comprising at least about 3% by weight of the dental bleaching composition, more preferably at least about 5% by weight of the bleaching composition, and most preferably at least about 7% by weight of the bleaching composition.

C. Rheology-Modifying Agents

A relatively small quantity of an inorganic, particulate rheology-modifying agent is included within the dental bleaching compositions of the invention to improve the rheological properties of the compositions. According to one embodiment, the rheology-modifying agent is included to offset the stringiness imparted by high molecular weight PVP and/or PEO and also to reduce or eliminate runniness. The rheology-modifying agent imparts greater internal cohesiveness of the composition, which reduces the tendency of the composition to otherwise break into many small filaments or threads (e.g., similar to a spider web) during handling (e.g., placement of the composition adjacent to a barrier layer).

The rheology-modifying agent also increases the Binghamian plastic properties of the composition, which reduces the tendency to run from where applied to the barrier layer. In other words, inclusion of fumed silica and/or fumed alumina results in a composition having a minimum yield stress, such that the composition has Bingham plastic flow characteristics. This advantageously allows the composition to be placed against the barrier layer and remain there, rather than running off the edge or running together, resulting in a relatively thick pool of the composition.

The ability of the rheology-modifying agent to increase the Binghamian plastic properties of a dental bleaching composition is not affected by high concentrations of peroxide dental bleaching agent. Thus, the rheology-modifying agent is able to impart long-term rheological stability in order to offset the tendency of polymeric tissue adhesion agent to lose viscosity and yield stress over time when exposed to high concentrations (e.g., 15% by weight or above) of a peroxide dental bleaching agent. This permits or causes the dental bleaching composition to remain in place next to the barrier layer where placed so that it does not run off the barrier layer in the short run or over a long period of time (e.g., at least about 3 months). This benefit is provided regardless of the polymeric thickening agent that is used.

A currently preferred rheology-modifying agent is fumed silica, which comprises submicron sized particles. Fumed silica is characterized as having a particle diameter of about 0.04 micron to about 0.1 micron. An example of a suitable fumed silica is AEROSIL 200, made by Degussa of Germany. Other sub-micron particulate rheology-modifying agents that may be used within the scope of the invention include fumed alumina, barium oxide, strontium oxide, titanium dioxide, and zirconium dioxide. Fumed silica is preferred because it is the most stable when used in a dental bleaching composition. Fumed alumina is somewhat less stable than fumed silica. Other sub-micron sized particulate rheology-modifying agents can be used, especially when long-term stability is less of an issue.

In order to offset stringiness and reduce runniness of dental bleaching compositions that include high molecular weight PVP and/or PEO, fumed silica, fumed alumina or other sub-micron rheology-modifying agents may be included in a broad range of about 1% to about 25% by weight of the dental bleaching composition. Nevertheless, because of the tendency of fumed silica or other particulate rheology-modifying agents to bind water, thereby potentially reducing bleaching activity, it will be preferable to include not more than about 8.5% fumed silica or fumed alumina. The amount of fumed silica or other rheology-modifying agent is preferably included in an amount in a range of about 1% to about 8.5%, more preferably in a range of about 2% to about 7.5%, and most preferably in a range of about 3% to about 6.5%.

D. Solvents and Carriers

The dental bleaching compositions also include at least one type of solvent or carrier in order to yield a gel composition having the desired rheological properties of stickiness (imparted mainly by the tissue adhesion agent) and Binghamian plastic properties (imparted mainly by the rheology-modifying agent). The solvent or carrier, typically a liquid at least initially, is what allows the tissue adhesion agent and rheology modifying agent to exhibit their desired rheological properties (i.e., the desired properties do not occur in a vacuum but in the context of being mixed with an appropriate solvent or carrier). Thus, a solvent or carrier is typically necessary to form an adhesive gel rather than a solid composition.

Whether the carrier is also a solvent depends on the interaction of a particular component with the carrier. For example, PVP and/or PEO may be at least partially soluble in water, glycerin or other carrier liquid, which make such carrier liquid a "solvent". On the other hand, particulate rheology-modifying agents such as fumed silica and fumed alumina are typically not dissolved in the carrier liquid but form a colloidal suspension. In such cases, the carrier is not a "solvent" insofar as the particulate rheology-modifying agent is concerned. On the other hand, the carrier may in fact be a solvent for an organic polymer rheology-modifying agent (e.g., guar gum or carboxymethyl cellulose).

Examples of suitable solvent or carrier liquids include, but are not limited to, water, glycerin, liquid polyethylene glycol (e.g., MW of about 600), propylene glycol, 1,3-propane diol, and other polyols known in the art.

The solvent or carrier may be included in any amount in order to yield dental bleaching compositions having the desired rheological properties. In general, the solvent or carrier will comprise the balance of the composition after adding the dental bleaching agent, tissue adhesion agent, rheology-modifying agent, and any optional components such as flavorants, bleaching agent stabilizers, neutralizing/buffering agents, remineralizing agents, desensitizing agents, and the like.

E. Other Components

The composition may include various other components to yield compositions having desired properties. Examples of other components include, but are not limited to, plasticizers and humectants (e.g., sorbitol), volatile solvents (e.g., alcohols such as ethanol), stabilizing agents (e.g., EDTA), neutralizing agents (e.g., sodium hydroxide), buffering agents (e.g., sodium phosphate and citric acid) desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

III. Dental Bleaching Devices

Dental bleaching devices within the scope of the invention include a dental bleaching composition, as discussed above, and a barrier layer that provides moisture resistance when the composition is placed over a person's teeth during dental bleaching.

A. Barrier Layers

According to one embodiment of the invention, the barrier layer comprises a thin, flexible membrane formed from a moisture-resistant polymer material. In a currently preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Notwithstanding the foregoing, it is within the scope of the invention to provide barrier layers of any desired material, thickness or rigidity so long as the barrier layer provides at least some moisture protection relative to the bleaching composition. The barrier layer may comprise a conventional dental tray, examples of which include both customized and non-custom dental trays. The barrier layer may alternatively comprise a flexible strip of material have no permanent shape or shape memory.

Examples of suitable polyolefins for use in making the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. Plasticizers, flow additives, and fillers known in the art can be used as desired to modify the properties of any of the foregoing polymers used to form the barrier layer.

In general, dental trays that may be used within the scope of the invention will preferably have a wall thickness of less than about 1.8 mm, more preferably less than about 1.5 mm, and most preferably less than about 1 mm. Flexible strips for use in making bleaching strips will preferably have a cross-sectional thickness less than about 1 mm, more preferably less than about 0.5 mm, and most preferably less than about 0.2 mm.

In one embodiment, a tray-shaped barrier layer is preferred as it not only provides a barrier to protect the composition from the action of saliva or moisture found within the mouth, but it also is more easily placed over the teeth to be treated, readily covering the front, lingual, and interproximal spaces between adjacent teeth. Such a tray shaped barrier layer may advantageously be preloaded with the dental bleaching composition, further simplifying the process. Alternatively, a kit may be provided that includes a barrier layer separate from a dental bleaching composition, allowing the user to dispense the composition adjacent the barrier layer prior to use. In either case, such devices and kits may be particularly well suited for over-the-counter sale to people wanting to whiten their own teeth, without the need for visits to a dental practitioner, resulting in a significantly less expensive alternative with good results. It will be apparent to one skilled in the art that a tray shaped barrier layer may comprise a customized or non-customized tray, as the dental bleaching composition including high molecular weight PVP and/or PEO and at least one rheology-modifying agent will improve the overall effectiveness and ease of use of the composite device (i.e., the barrier layer and the bleaching composition).

B. Characteristics of Exemplary Dental Bleaching Devices

Exemplary dental bleaching devices may include a tray shaped barrier layer in different configurations for treatment of the upper and lower dental arches. The tray typically includes at least two walls. According to one embodiment, the tray includes a front side wall, a rear side wall, and a bottom wall. The tray may be shaped to cover at least a portion of the rear surfaces of the teeth, the incisal edges, and especially the front surface of the teeth, which is the surface that is most often seen (and therefore most desirable to whiten). The trays may be configured to cover any desired number of teeth. In one embodiment, the trays may be sized and configured to cover at least 8 of the front upper teeth and at least 8 of the front lower teeth, depending on the size of the tray, especially the tray's side walls, which provide treatment to the front and back surfaces of the teeth. Advantageously, the tray shaped barrier layer provides improved contact between the bleaching composition and the teeth, with improved contact of the bleaching composition to the interproximal spaces between teeth as compared to conventional bleaching strips. In this way, the margins between the teeth can be better bleached, compared to existing bleaching strip products, which only reliably treat the front tooth surfaces and only if they are able to remain in place and not become prematurely dislodged.

Referring now to the drawings, FIG. 1A illustrates an embodiment of a dental treatment device 100 configured for placement over a person's upper dental arch. The device 100 comprises a barrier layer configured as a non-custom pre-shaped dental tray 101 including a bottom wall 102 having a generally horseshoe-shaped configuration generally conforming to the size and shape of the person's upper dental arch. The bottom wall 102 of the illustrated embodiment has a generally flat profile, although it could have other shapes, as desired (e.g., curved). The barrier layer 101 further includes a front side wall 104 extending laterally from a front end of the bottom wall 102 and a rear side wall 106 extending laterally from a rear end of the bottom wall 102. Together, the bottom wall 102, front side wall 104, and rear side wall 106 form a tray shaped barrier layer 101 that includes a hollow interior portion, or trough, that is open at the top, and that terminates at open ends 108. Because barrier 101 is not customized, it lacks recesses corresponding to a person's unique dentition.

The front side wall 104 of the tray 101 may extend substantially perpendicularly relative to the bottom wall 102, particularly at the ends 108 of the tray, although it may extend at any desired angle so as to conform or correspond to a person's teeth in a desired manner. The front side wall 104 of the tray 101 is generally taller toward the middle where it corresponds to the middle teeth and generally shorter toward the ends 108. Thus, the front side wall 104 tapers from front to back in order to approximately correspond to the descending height of teeth from the middle of the dental arch (i.e., at the incisors) toward the rear of the dental arch (i.e., at the molars).

In one embodiment, the front side wall 104 may include a notch 105. The notch 105 allows the tray to more easily spread open and conform to larger dental arches compared to dental trays that do no include this notch. In this way, the barrier layer tray can comfortably and effectively fit a larger range of varyingly-sized dental arches. The notch 105 is preferably formed near the middle portion 110, preferably at the top or edge of front side wall 104. The rear side wall 106 may also include a notch 109 that is able to substantially perform the same function as notch 105.

Like the front side wall 104, the rear side wall 106 of the tray 100 may be shorter and substantially perpendicular to the bottom wall 102 at the ends 108 of the horseshoe-shaped tray 101, but gradually open up to form a more oblique angle near a middle curved portion 110 of the tray so as to better accommodate the roof of the mouth near the middle portion 110 of the tray 101. The height of the rear side wall 106 is generally shorter than the corresponding section of the front side wall 104, particularly near the middle portion 110. This difference in height is to accommodate the differing height of the front versus the rear surface of the teeth in addition to the lower roof of the mouth relative to the rear side wall 106.

The bottom wall 102 has a width near the curved middle portion 110 of the tray that is advantageously less than the width of the bottom wall 102 between the middle portion 110 and the ends 108 of the tray 101. This allows for differences in the radial width of a person's incisors and canines relative to the much wider bicuspids and molars. In one embodiment, the upper edges of front side wall 104 and rear side wall 106 are thickened and rounded. Rounding the edges of the tray may provide greater comfort for the wearer. Thickening the edges helps the barrier layer maintain structural integrity, particularly if the remainder of the tray is very thin.

FIG. 1A depicts a quantity of a dental bleaching composition 112 disposed within the hollow interior portion, or trough, of the tray 101 adjacent to the front wall 104. The composition 112 may alternatively be placed adjacent the bottom wall, the rear wall, or any combination thereof. The composition 112 includes a first surface disposed adjacent to an interior surface of the barrier layer 101 and an opposite second surface designed to directly contact a person's teeth when the device 100 is in use. When placed over a person's teeth, the dental bleaching composition 112 will advantageously contact and strongly adhere to at least the front surfaces of the person's teeth, providing a whitening treatment to the teeth.

Composition 112 may be placed and sized so as to rise about two-thirds of the height of front wall 104. Because the dental treatment composition 112 contains high molecular weight PVP and/or PEO (i.e., greater than about 500,000) and fumed silica or other rheology-modifying agent, the handling properties of the composition are greatly improved as compared to bleaching compositions that include PVP or PEO as sole tissue adhesion agent. In the case where any of PVP, PEO or carboxypllymethylene is used, the fumed silica or other rheology-modifying agent yields a composition having long-term rheological stability such that it will remain where placed adjacent to a barrier layer.

Figure 1B:
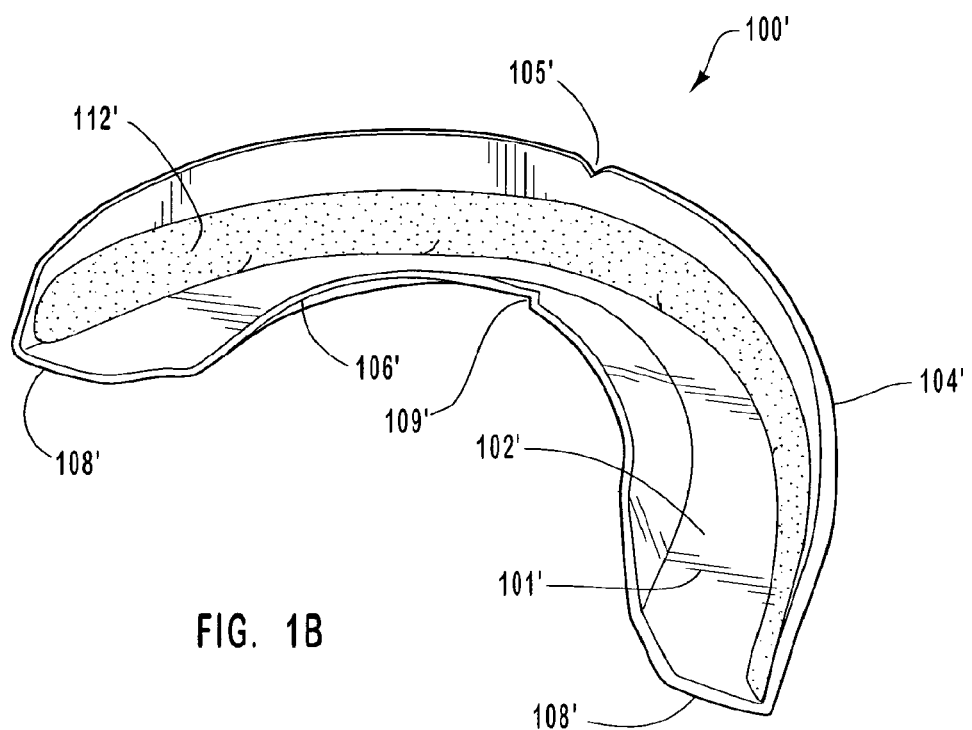
FIG. 1B is a perspective view of an exemplary embodiment of a dental treatment device configured for placement over the lower dental arch, the device including a barrier layer and a dental bleaching composition disposed adjacent to the barrier layer.

FIG. 1B illustrates an embodiment of a dental bleaching device 100' configured for placement over a person's lower dental arch. The device 100' includes a tray-shaped barrier layer 101' that comprises a bottom wall 102' having a generally horseshoe-shaped configuration generally conforming to the shape of the person's lower dental arch. The bottom wall 102' has a generally flat planar profile, although it could have other shapes if desired (e.g., curved). The dental tray 101' further includes a front side wall 104' extending laterally from a front end of the bottom wall 102' and a rear side wall 106' extending laterally from a rear end of the bottom wall 102'. Together, the bottom wall 102', front side wall 104', and rear side wall 106' form a tray shaped barrier layer 101' that includes a hollow interior portion, or trough, that is open at the top, and that terminates at open ends 108'. Both side walls 104' and 106' (especially front side wall 104') are shorter than corresponding side walls 104 and 106 because of the generally smaller size of the lower teeth versus the upper teeth. The tray 101' may include notches 105' and 109'. A quantity 112' of a dental bleaching composition is shown in the hollow interior portion, or trough, of the tray 101', adjacent to front side wall 104'.

Figure 2:
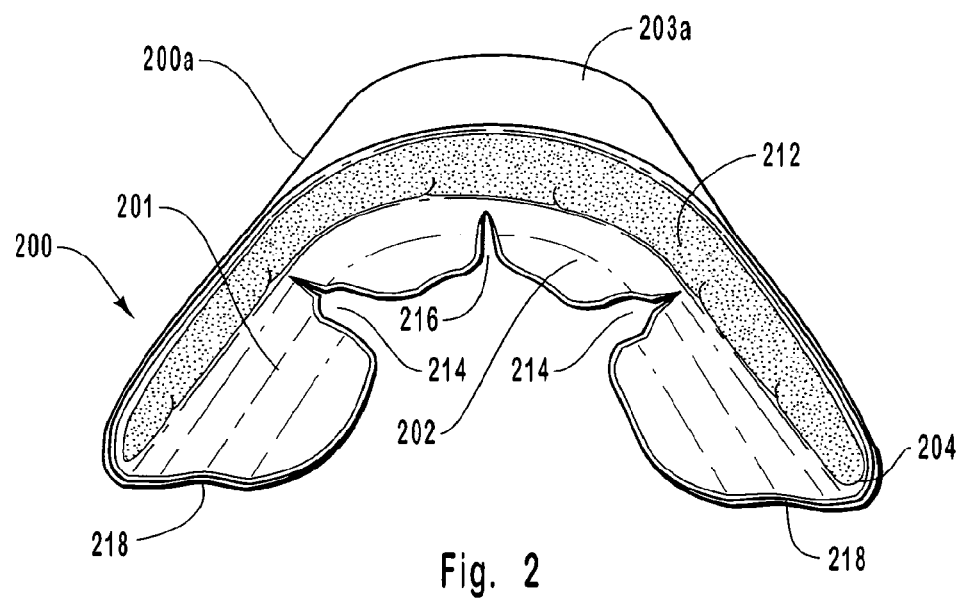
FIG. 2 is a perspective view of an alternative embodiment of another dental treatment device including a tray-shaped barrier layer and a dental bleaching composition disposed adjacent to the barrier layer.

FIG. 2 illustrates another dental bleaching device 200 including a moisture-resistant barrier layer 201 having a bottom wall 202 and a front side wall 204. Bottom wall 202 includes notches 214 in the bottom wall 202 positioned so as to help the bottom wall 202 better conform to abrupt changes in the diameter of a person's teeth, particularly where the bicuspids and canines meet. Bottom wall 202 also includes an additional notch 216, which allows the barrier layer 201 to more easily spread open or compress in the area of the incisors so as to more easily conform to differently-sized dental arches. The bottom wall 202 also includes two V-shaped indentations 218 configured to be inserted into the depressions typically found along the top surfaces of a person's left and right molars. The bleaching device 200 also includes a bleaching composition 212 disposed adjacent the front side wall 204 of barrier layer 201. Because the dental bleaching composition 212 contains high molecular weight PVP and/or PEO (i.e., greater than about 500,000) and fumed silica or other rheology-modifying agent, the handling properties of the composition are greatly improved as compared to bleaching compositions that include PVP or PEO as the sole tissue adhesion agent. In the case where any of PVP, PEO or carboxypllymethylene is used, the fumed silica or other rheology-modifying agent yields a composition having long-term rheological stability such that it will remain where placed adjacent to a barrier layer.

As illustrated, the device 200 may be held within an exoskeleton 200a, which may be advantageous during placement of the device over a person's teeth, particularly in the instance where exoskeleton 200a includes a handle 203a for the user to grip during placement. Once positioned over the teeth as desired, the exoskeleton 200a may be discarded, leaving just the barrier layer and composition adhered to the dental arch. Additional disclosure regarding barrier layers and exoskeletons as illustrated in FIG. 2 is contained in U.S. Pat. No. 7,059,858, entitled UNIVERSAL TRAY DESIGN HAVING ANATOMICAL FEATURES TO ENHANCE FIT, hereby incorporated by reference with respect to its disclosure of barrier layers, exoskeletons, and dental treatment devices.

Figure 3:
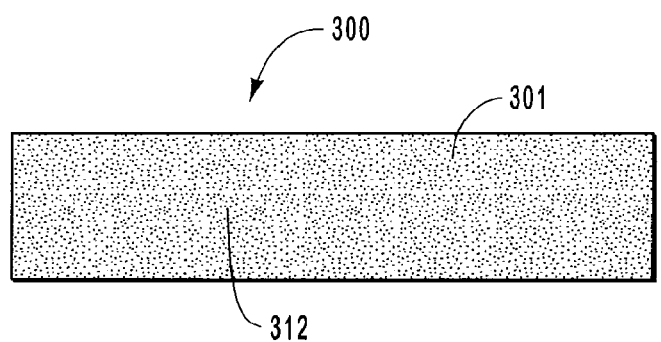
FIG. 3 is a perspective view of another dental treatment device including a barrier layer configured as an initially flat strip and a dental bleaching composition disposed adjacent to the barrier layer.

FIG. 3 illustrates another dental treatment device 300. Dental treatment device 300 includes a barrier layer 301 configured as a strip that has no predefined shape but that is initially substantially flat as a result of how it is packaged, and a quantity of dental bleaching composition 312 disposed adjacent a surface of strip 301. Strip 301 may be placed over a person's teeth, and then a portion of the strip 301 may be folded over the occlusal surface of the covered teeth so as to effect bleaching.

Although a strip configuration may be less preferred, the presence of the composition 312 including high molecular weight PVP and/or PEO and at least one rheology-modifying agent, such as fumed silica, provides the device 300 with improved properties as compared to existing dental bleaching strips. For example, the inclusion of PVP and/or PEO having a molecular weight of greater than about 500,000 greatly improves the adhesive properties of the composition, allowing the device to be placed over and reliably adhere to the teeth. Furthermore, the rheology-modifying agent provides improved handling properties as described above. In the case where any of PVP, PEO or carboxypllymethylene is used, the fumed silica or other rheology-modifying agent yields a composition having long-term rheological stability such that it will remain where placed adjacent to a barrier layer.

The result is a greatly improved bleaching strip that adheres very well to the teeth, even if two strips are placed on the top and bottom dental arches simultaneously, and/or while engaging in various activities that have been found to result in dislodgement of conventional bleaching strips (e.g., talking, sleeping, eating, drinking, smiling, frowning, grimacing, yawning, coughing, smoking, kissing, or making virtually any facial expression or mouth contortion). This greatly decreases their intrusiveness into everyday activities compared to conventional bleaching strips, which do not reliably adhere to teeth.

Figure 4:
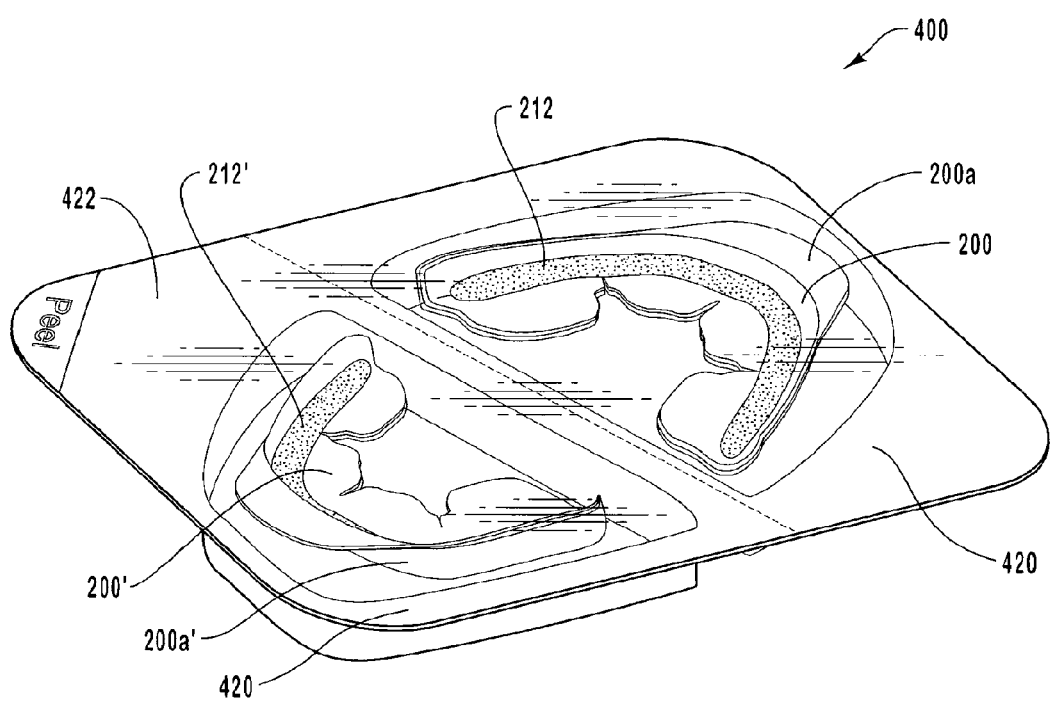
FIG. 4 illustrates two dental bleaching devices similar to that illustrated in FIG. 2, the devices being contained within a sealed packaging container.

In order to protect the bleaching device, particularly the bleaching composition, from contaminants during storage and prior to use, one or more of the devices can be packaged within a sealed container or package. As illustrated in FIG. 4, devices 200 and 200', along with associated exoskeletons 200a and 200a' respectively, can be sealed within a protective package 400. In one example, device 200 may be configured for placement over the upper dental arch while device 200' may be configured for placement over the lower dental arch. Package 400 includes a rigid support layer 420 and a peelable cover 422. Although illustrated with dental bleaching device 200 and 200', it is to be understood that any device embodiment including a barrier layer and a dental bleaching composition comprising a tissue adhesion agent and a rheology-modifying agent as discussed herein can be sealed within a protective package.

When it is desired to use devices 200 and 200', the peelable cover 422 is removed and the bleaching devices are removed or separated from the support layer 420. In addition to, or instead of, the protective package 400, the dental treatment devices may alternatively each include a removable protective layer (not shown) that is temporarily placed adjacent to the interior surface of the dental bleaching composition 212, 212'. When it is desired to use the dental treatment device, the removable protective layer is removed so as to expose the interior surface of the dental bleaching composition 212 or 212'. Alternatively, the dental bleaching composition may be provided in a separate container (e.g., a squeeze tube, not shown) and dispensed adjacent to the barrier layer (e.g., within the trough of a tray shaped barrier layer) by the user just prior to use.

Notwithstanding the foregoing, it should be understood that the barrier layer, within the scope of the invention, can have any desired configuration such that the trays and strips of FIGS. 1-4 are merely illustrative, non-limiting examples of barrier layers and devices configured for placement over the upper or lower dental arch.

IV. Exemplary Methods of Use

Figure 5A:
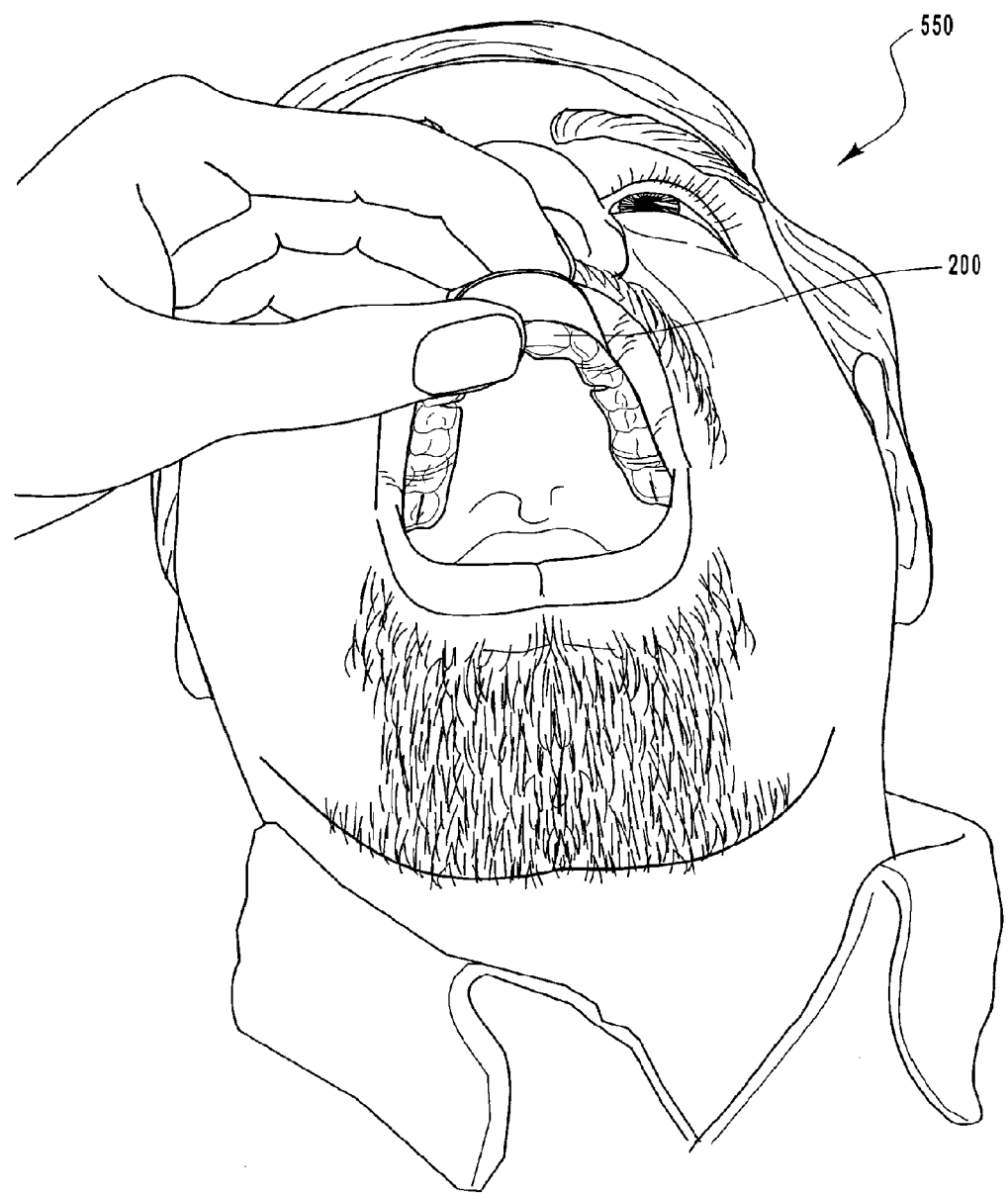
FIG. 5A illustrates a person placing a dental bleaching device according to the invention over the upper dental arch.
Figure 5B:
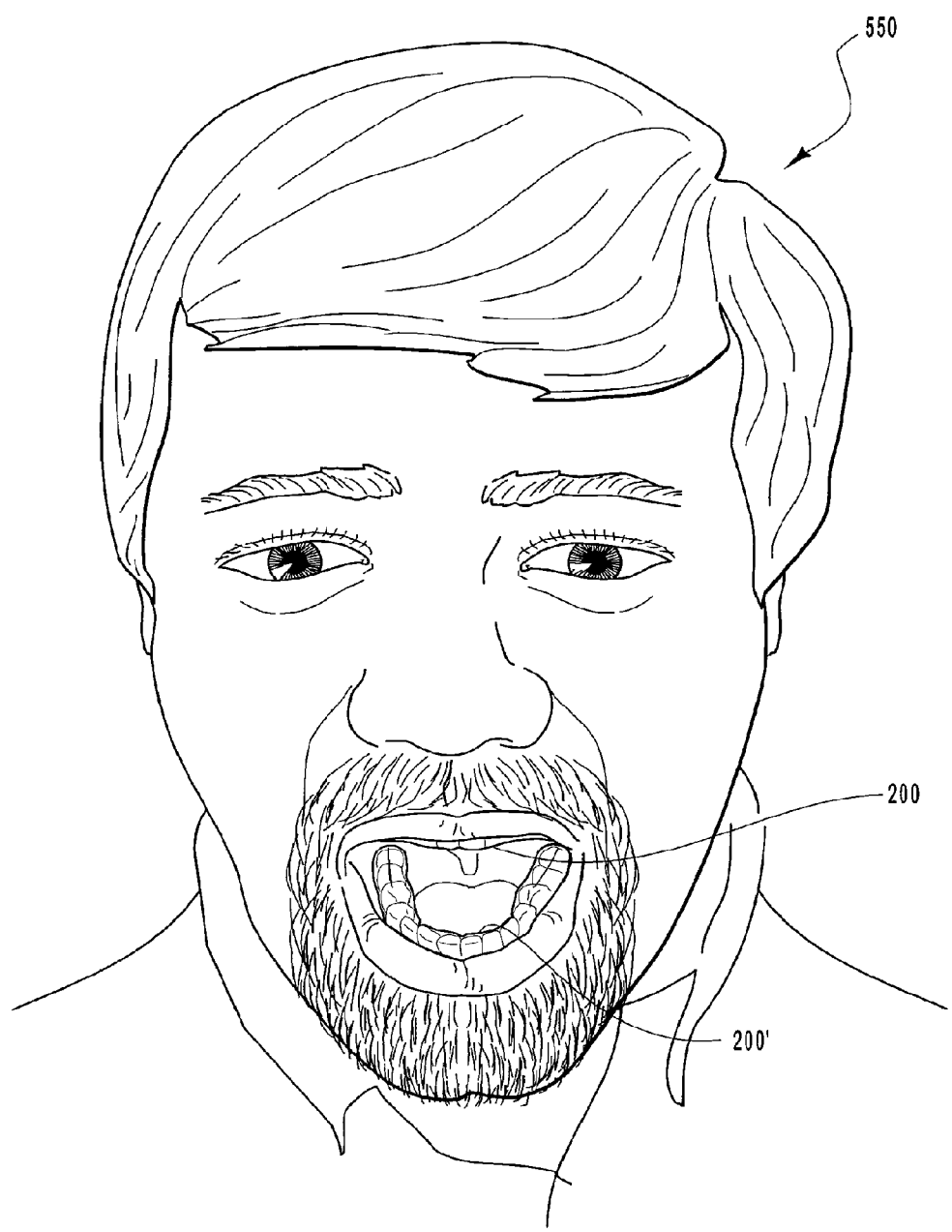
FIG. 5B illustrates a person after placing dental treatment devices over the upper and lower dental arches.

FIGS. 5A-5B illustrate trays 200 and 200' (e.g., those within the package of FIG. 4) being placed by the user 550 over his or her upper and lower dental arches. Tray 200 is filled with a dental bleaching composition 212 (as seen in FIG. 4), which was either preloaded in the tray or placed in the tray just prior to use. As illustrated in FIG. 5A, the user 550 is easily able to place the tray 200 over the upper dental arch. The presence of high molecular weight PVP (or PEO) and/or carboxypolymethylene within bleaching composition 212 causes the composition to reliably adhere to the teeth, maintaining contact between the teeth to be bleached and the bleaching agent within bleaching composition 212.

FIG. 5B illustrates a tray 200' being placed by the user 550 over his or her lower dental arch, optionally with the tray 200 as seen in FIG. 5A in place over the upper dental arch. The tray is filled with a dental bleaching composition that was either preloaded in the tray or placed in the tray just prior to use. The user 550 is easily able to place the device 200 over the lower dental arch, even while device 200 is in position over the upper dental arch.

To remove the bleaching devices, a user can pry open a corner of the barrier layer using a fingernail or rigid tool and then pull the remainder off. Any residual bleaching composition that remains adhered to the person's teeth can be removed by washing or flushing water over the person's teeth, and/or by brushing. Although the dental bleaching compositions including high molecular weight PVP (or PEO) and/or carboxypolymethylene are very adhesive to teeth when protected from excessive moisture, they can be formulated to quickly break down and dissolve when flushed with excess water and/or by gentle mechanical action (e.g., brushing).

The dental bleaching devices can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. A typical bleaching regimen will preferably include 1-20 bleaching sessions, more preferably 2-15 bleaching sessions, and most preferably 3-10 bleaching sessions.

V. Exemplary Bleaching Kits

It is within the scope of the invention to provide barrier layers and a bleaching composition that are initially separate and that are brought together by the end user. Such a kit may include one or more tray shaped or other barrier layers and the dental bleaching composition. The user is able to dispense a quantity of the dental bleaching composition adjacent the barrier layer prior to use. The use of the dental bleaching composition including high molecular weight PVP and/or PEO and at least one rheology-modifying agent (e.g., fumed silica) is particularly advantageous as it improves the handling properties of the composition, making it much easier for the user to dispense the composition in a desired quantity and in a coherent mass (or a small number of coherent masses). For example, if dispensed from a squeeze tube or syringe, the composition tends to dispense as a single coherent mass, which can be cut off at the dispensing tip or nozzle with little risk that the composition will break apart into a stringy mess.

Furthermore, because the dental bleaching composition includes a quantity of PVP and/or PEO having a molecular weight greater than about 500,000 it is very tacky and adhesive when contacted by tooth tissue. The PVP and/or PEO act to hold the device against the user's teeth, and also to cause the barrier layer to at least partially conform to the user's teeth. In this way, the devices can be used to treat a wide variety of differently sized dental arches and teeth among different users without having to form a customized dental tray, as is commonly done for home bleaching regimens.

VI. Examples

The following are several examples of bleaching compositions. Such exemplary compositions are given by way of example, and not by limitation, in order to illustrate dental bleaching compositions according to the invention. Unless otherwise indicated, all percentages are by weight.

Comparative Example 1

A dental bleaching composition was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F (PVP 1.3 million MW) | 10% |
| Peach Flavor | 3% |
| Sucralose (25% in water) | 3% |

The resulting dental bleaching composition was very tacky and adhesive to teeth but somewhat difficult to handle. A quantity of the composition was placed within a flexible, thin-walled dental tray and then placed over a person's teeth. During handling, the composition tended to run due to low viscosity, making it difficult to place the dental composition into the tray without creating a mess. Although the composition was difficult to handle, it was able to adhere and retain the flexible, thin-walled dental tray very well against the person's teeth for a desired period of time (e.g., 1 hour or more). The viscosity and runniness worsened over time, presumably due to the effect of the peroxide bleaching agent on the polymeric thickening agents over time.

Comparative Example 2

A dental bleaching composition was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F (PVP 1.3 million MW) | 2% |
| Carboxy Methyl Cellulose | 4% |
| Peach Flavor | 3% |

The resulting dental bleaching composition was tacky and adhesive to teeth but difficult to handle. A quantity of the composition was placed within a flexible, thin-walled dental tray and then placed over a person's teeth. During handling, the composition tended to run due to low viscosity, making it difficult to place the dental composition into the tray without creating a mess. Although the composition was difficult to handle, it was able to adhere and retain the flexible, thin-walled dental tray very well against the person's teeth for a desired period of time (e.g., 1 hour or more). The viscosity and runniness worsened over time, presumably due to the effect of the peroxide bleaching agent on the polymeric thickening agents over time.

Comparative Example 3

A dental bleaching composition is formed by mixing together the following components:

| | |
|---|---|
| Carbamide Peroxide | 10% |
| Water | 21% |
| Ethanol | 16% |
| PVP (M.W. = 300,000) | 20% |
| Glycerin | 28% |
| PEG 600 | 5% |

The resulting dental bleaching composition is adhesive to teeth but also difficult to handle because of its tendency to run due to low viscosity and its tendency to break into dozens of tiny threads, making it difficult to place into tray without creating a mess. A quantity of the composition is placed within a flexible, thin-walled dental tray and then placed over a person's teeth. Although the composition is difficult to handle, it is able to adhere and retain the flexible, thin-walled dental tray against a person's teeth for a desired time period (e.g., 1 hour or more).

Example 4

A dental bleaching composition is formed by mixing together the following components:

| | |
|---|---|
| Calcium Peroxide | 10% |
| Water | 20% |
| Ethanol | 21% |
| PVP (M.W. = 500,000) | 20% |
| Glycerin | 24% |
| Fumed Silica | 5% |

The resulting dental bleaching composition is significantly more tacky and adhesive than the composition of Comparative Example 3 as a result of including PVP having a molecular weight of 500,000, while also having improved handling properties as compared to Examples 1-3 as a result of the inclusion of fumed silica. A quantity of the composition is placed adjacent a barrier layer and then placed over a person's teeth. During handling, the composition exhibits a sufficiently high yield stress that prevents the composition from running off the edge of the barrier layer. In addition, the composition tends to hold together as a single coherent mass, making it relatively simple to place the composition into the tray without stringiness. The composition is able to adhere and retain the flexible, thin-walled dental tray against the person's teeth for a desired period of time (e.g., 1 hour or more). The composition has excellent long-term rheological stability.

Example 5

A dental bleaching composition is formed by mixing together the following components:

| | |
|---|---|
| Calcium Peroxide | 10% |
| Water | 20% |
| Ethanol | 16% |
| PVP (M.W. = 650,000) | 20% |
| Glycerin | 29% |
| Fumed Silica | 5% |

The resulting dental bleaching composition is even more tacky and adhesive than the composition of Example 4, while also having improved handling properties as compared to Examples 1-3. A quantity of the composition is placed adjacent a barrier layer and then placed over a person's teeth. During handling, the composition exhibits a sufficiently high yield stress that prevents the composition from running off the edge of the barrier layer. In addition, the composition tends to hold together as a single coherent mass, making it relatively simple to place the composition into the tray without creating a mess. The composition is able to adhere and retain the flexible, thin-walled dental tray against the person's teeth for a desired period of time (e.g., 1 hour or more). The composition has excellent long-term rheological stability.

Example 6

A dental bleaching composition is formed by mixing together the following components:

| | |
|---|---|
| Calcium Peroxide | 10% |
| Water | 20% |
| Ethanol | 21% |
| PVP (M.W. = 800,000) | 15% |
| Glycerin | 29% |
| Fumed Silica | 5% |

The resulting dental bleaching composition exhibits excellent tackiness and adhesiveness even with a lower quantity of PVP than Examples 3-5, while also having improved handling properties as compared to Examples 1-3. A quantity of the composition is placed adjacent a barrier layer and then placed over a person's teeth. During handling, the composition exhibits a sufficiently high yield stress that prevents the composition from running off the edge of the barrier layer. In addition, the composition tends to hold together as a single coherent mass, making it relatively simple to place the composition into the tray without creating a mess. The composition is able to adhere and retain the flexible, thin-walled dental tray against the person's teeth for a desired period of time (e.g., 1 hour or more). The composition has excellent long-term rheological stability.

Example 7

A dental bleaching composition was formed by mixing together the following components:

| | |
|---|---|
| Water | 10% |
| EDTA Disodium | 0.1% |
| Hydrogen Peroxide (35% solution) | 32% |
| Glycerin | 39.35% |
| PVP (1.3 million MW) | 15% |
| Sucralose (25% in water) | 0.25% |
| Peppermint Oil | 0.3% |
| Aerosil 200 (fumed silica) | 3% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 8

A dental bleaching composition was formed by mixing together the following components:

| | |
|---|---|
| Water | 10% |
| EDTA Disodium | 0.1% |
| Hydrogen Peroxide (35% solution) | 32% |
| Glycerin | 34.35% |
| PVP (1.3 million MW) | 15% |
| Sucralose (25% in water) | 0.25% |
| Peppermint Oil | 0.3% |
| Aerosil 200 (fumed silica) | 8% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 9

A dental bleaching composition was formed by mixing together the following components:

| | |
|---|---|
| Water | 10% |
| EDTA Disodium | 0.1% |
| Hydrogen Peroxide (35% solution) | 32% |
| Glycerin | 32.35% |
| PVP (1.3 million MW) | 22% |
| Sucralose (25% in water) | 0.25% |
| Peppermint Oil | 0.3% |
| Aerosil 200 (fumed silica) | 3% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 10

A dental bleaching composition was formed by mixing together the following components:

| | |
|---|---|
| Water | 10% |
| EDTA Disodium | 0.1% |
| Hydrogen Peroxide (35% solution) | 32% |
| Glycerin | 30.35% |
| PVP (1.3 million MW) | 22% |
| Sucralose (25% in water) | 0.25% |
| Peppermint Oil | 0.3% |
| Aerosil 200 (fumed silica) | 5% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 11

A dental bleaching composition was formed by mixing together the following components:

| | |
|---|---|
| Water | 14.9% |
| EDTA Disodium | 0.1% |
| Hydrogen Peroxide (35% solution) | 16.44% |
| Glycerin | 20.39% |
| PVP (1.3 million MW) | 20% |
| Sucralose (25% in water) | 0.5% |
| Peppermint Oil | 0.3% |
| Aerosil 200 (fumed silica) | 8% |
| Carbamide Peroxide | 9.27% |
| Xylitol | 10% |
| Sodium Hydroxide | 0.1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 12

A dental bleaching composition was formed by mixing together the following components:

| | |
|---|---|
| Water | 14.9% |
| EDTA Disodium | 0.1% |
| Hydrogen Peroxide (35% solution) | 16.44% |
| Glycerin | 17.39% |
| PVP (1.3 million MW) | 27% |
| Sucralose (25% in water) | 0.5% |
| Peppermint Oil | 0.3% |
| Aerosil 200 (fumed silica) | 4% |
| Carbamide Peroxide | 9.27% |
| Xylitol | 10% |
| Sodium Hydroxide | 0.1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 13

A dental bleaching composition was formed by mixing together the following components:

| | |
|---|---|
| Water | 10.1% |
| EDTA Disodium | 0.1% |
| Hydrogen Peroxide (35% solution) | 19.5% |
| Glycerin | 25.2% |
| PVP (1.3 million MW) | 15% |
| Sucralose (25% in water) | 0.5% |
| Peppermint Oil | 0.5% |
| Aerosil 200 (fumed silica) | 8% |
| Carbamide Peroxide | 11% |
| Xylitol | 10% |
| Sodium Hydroxide | 0.1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 14

A dental bleaching composition was formed by mixing together the following components:

| | |
|---|---|
| Water | 14.89% |
| EDTA Disodium | 0.1% |
| Hydrogen Peroxide (35% solution) | 16.44% |
| Glycerin | 24.7% |
| PVP (1.3 million MW) | 15% |
| Sucralose (25% in water) | 0.5% |
| Peppermint Oil | 0.5% |
| Aerosil 200 (fumed silica) | 8.5% |
| Carbamide Peroxide | 9.27% |
| Xylitol | 10% |
| Sodium Hydroxide | 0.1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 15

A dental bleaching composition was formed by mixing together the following components:

| | |
|---|---|
| Water | 10.1% |
| EDTA Disodium | 0.1% |
| Hydrogen Peroxide (35% solution) | 19.5% |
| Glycerin | 24.2% |
| PVP (1.3 million MW) | 15% |
| Sucralose (25% in water) | 0.5% |
| Peppermint Oil | 0.5% |
| Aerosil 200 (fumed silica) | 8% |
| Carbamide Peroxide | 11% |
| Xylitol | 10% |
| Sodium Hydroxide | 0.1% |
| Carboxymethyl Cellulose | 1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 16

A dental bleaching composition was formed by mixing together the following components:

| | |
|---|---|
| Water | 14.9% |
| EDTA Disodium | 0.1% |
| Hydrogen Peroxide (35% solution) | 16.44% |
| Glycerin | 23.39% |
| PVP (1.3 million MW) | 20% |
| Sucralose (25% in water) | 0.5% |
| Peppermint Oil | 0.3% |
| Aerosil 200 (fumed silica) | 5% |
| Carbamide Peroxide | 9.27% |
| Xylitol | 10% |
| Sodium Hydroxide | 0.1% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 17

A dental bleaching composition was formed by mixing together the following components:

| | |
|---|---|
| Water | 19% |
| EDTA Disodium | 0.1% |
| Hydrogen Peroxide (50% solution) | 18% |
| Glycerin | 36.93% |
| PVP (1.3 million MW) | 15% |
| Sucralose (25% in water) | 0.3% |
| Peppermint Oil | 0.4% |
| Aerosil 200 (fumed silica) | 9.5% |
| Sodium Fluoride | 0.25% |
| Potassium Nitrate | 0.5% |

The resulting dental bleaching composition was very tacky, adhesive, and could be handled with considerable ease as compared to the compositions of Examples 1-3. A quantity of the composition was placed adjacent a barrier layer and then placed over a person's teeth. During handling, the composition exhibited a sufficiently high yield stress that prevented the composition from running off the edge of the barrier layer. In addition, the composition tended to hold together as a single coherent mass, making it relatively simple to place the composition into the tray without creating a mess. The composition was able to adhere and retain the flexible, thin-walled dental tray against the person's teeth for a desired period of time (e.g., 1 hour or more). The composition exhibited excellent long-term rheological stability.

Example 18

Any of Examples 4-17 is modified by replacing the PVP with an equal quantity of PEO having the same molecular weight. The rheology-modifying agent greatly improves handling properties and long-term rheological stability compared to the compositions of Comparative Examples 1-3.

Example 19

A dental bleaching composition is formed by mixing together the following components:

| | |
|---|---|
| Hydrogen Peroxide (50% solution) | 20% |
| Water | 20% |
| Carbopol 974 (carboxypolymethylene) | 8% |
| Sodium Hydroxide (50% solution) | 4.5% |
| Glycerin | 41% |
| Fumed Silica | 6% |
| Potassium Nitrate | 0.5% |

The resulting dental bleaching composition is very tacky and adhesive, while also having improved long-term rheological stability as compared to Examples 1-3 or the composition of this example without fumed silica. A quantity of the composition is placed adjacent a barrier layer and then placed over a person's teeth. During handling, the composition exhibits a sufficiently high yield stress that prevents the composition from running off the edge of the barrier layer. The composition is able to adhere and retain the flexible, thin-walled dental tray against the person's teeth for a desired period of time (e.g., 1 hour or more).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a dental bleaching device comprising:
    providing a dental bleaching composition that is sticky and adhesive to teeth comprising:
        at least 5% by weight of a dental bleaching agent;
        at least 5% by weight of a tissue adhesion agent comprising one or more high molecular weight linear polymers;
        a rheology-modifying agent comprising an inorganic particulate; and
        a carrier comprising water and at least one of a polyol or glycerin;
    dispensing a quantity of the dental bleaching composition from a dispensing apparatus onto a barrier layer; and
    separating the dispensing apparatus from the quantity of the dental bleaching composition without substantially forming elongated strings of the dental bleaching composition.

2. The method of claim 1, the dental bleaching composition being dispensed onto the barrier layer as a single coherent mass and then severed from the dispensing apparatus without forming spider web-like strings.

3. The method of claim 1, the rheology-modifying agent reducing or eliminating stringiness otherwise caused by the tissue adhesion agent in the absence of the rheology-modifying agent.

4. The method of claim 1, dispensing apparatus comprising a tip, nozzle, syringe, or squeeze tube.

5. The method of claim 1, the barrier being in the form of a strip or tray, the method yielding a dental bleaching strip or dental bleaching tray.

6. The method of claim 1, the barrier layer comprising at least one material selected from the group consisting of polyolefins, polyethylene (PE), high density polyethylene (HDPE), low density polyethylene (LDPE), ultra low density polyethylene (ULDPE), polypropylene (PP), polytetrafluoroethylene (PTFE), waxes, metal foils, ethylene-vinyl acetate copolymer (EVA), ethylene-vinyl alcohol copolymer (EVAL), polycaprolactone (PCL), polyvinyl chloride (PVC), polyesters, polyethylene terephthalate (PET), polycarbonates, polyamides, polyurethanes, and polyesteramides.

7. The method of claim 1, the barrier layer comprising paraffin wax.

8. The method of claim 1, the dental bleaching agent comprising a peroxide.

9. The method of claim 1, the dental bleaching agent being included in a range of about 10% to about 60% by weight of the dental bleaching composition.

10. The method of claim 1, the one or more high molecular weight linear polymers comprising at least one of polyvinyl pyrrolidone (PVP) or polyethylene oxide (PEO).

11. The method of claim 10, the PVP and/or PEO having a molecular weight of at least 500,000.

12. The method of claim 10, the PVP and/or PEO having a molecular weight of at least 800,000.

13. The method of claim 1, the tissue adhesion agent being included in an amount of at least 10% by weight of the dental bleaching composition.

14. The method of claim 1, the tissue adhesion agent being included in an amount in a range of about 15% to about 25% by weight of the dental bleaching composition.

15. The method of claim 1, the rheology-modifying agent increasing long-term rheological stability of the dental bleaching composition.

16. The method of claim 1, the rheology-modifying agent comprising at least one of fumed silica or fumed alumina.

17. The method of claim 16, the fumed silica and/or fumed alumina being included in an amount in a range of about 3% to about 6.5% by weight of the dental bleaching composition.

18. The method of claim 1, the carrier further comprising at least one polyol selected from the group consisting of liquid polyethylene glycol, propylene glycol, 1,3-propanediol, and mixtures thereof.

19. The method of claim 1, the dental bleaching composition comprising an adhesive gel.

20. The method of claim 1, the carrier further comprising one or more volatile solvents, the method further comprising removing the one or more volatile solvents to form a solid bleaching composition.

21. A method of manufacturing a dental bleaching device comprising:
    providing a dental bleaching composition that is sticky and adhesive to teeth comprising:
        at least 5% by weight of a dental bleaching agent;
        at least 5% by weight of a tissue adhesion agent comprising polyvinyl pyrrolidone (PVP) and/or polyethylene oxide (PEO) having a molecular weight of at least 500,000;
        an inorganic particulate; and
        a liquid carrier into which the dental bleaching agent, PVP and inorganic particulate are dispersed;
    dispensing a coherent mass of the dental bleaching composition from a dispensing apparatus onto a barrier layer; and
    removing the dispensing apparatus from the coherent mass of the dental bleaching composition to separate the coherent mass from the remaining dental bleaching composition without substantially forming elongated strings.

22. The method of claim 21, the PVP and/or PEO having a molecular weight of at least 1,000,000.

23. The method of claim 21, the liquid carrier comprising water and at least one of glycerin, liquid polyethylene glycol, propylene glycol, or 1,3-propanediol.

24. The method of claim 21, the inorganic particulate being included in an amount in a range of about 3% to about 6.5% by weight of the dental bleaching composition.

25. A method of manufacturing a dental bleaching tray comprising:
    providing a dental bleaching composition that is sticky and adhesive to teeth comprising:
        at least 5% by weight of a dental bleaching agent;
        about 15% to about 25% by weight of polyvinyl pyrrolidone (PVP);
        about 3% to about 6.5% fumed silica; and
        a liquid carrier into which the dental bleaching agent, PVP and inorganic particulate are dispersed, the liquid carrier comprising water and at least one of glycerin or a polyol;
    dispensing a coherent mass of the dental bleaching composition from a dispensing apparatus into a dental tray; and
    severing the dental bleaching composition remaining with the dispensing apparatus from the coherent mass of the dental bleaching composition in the dental tray without substantially forming elongated strings.

\* \* \* \* \*